United States Patent [19]

Matsuo

[11] Patent Number: 5,352,770
[45] Date of Patent: Oct. 4, 1994

[54] PORCINE DERIVED NOVEL PHYSIOLOGICALLY ACTIVE PEPTIDE

[76] Inventor: Hisayuki Matsuo, 4-24-204, Nishiokamoto 6-chome, Higashinada-ku, Kobe-shi, Hyogo-ken, Japan

[21] Appl. No.: 778,847
[22] PCT Filed: Apr. 20, 1991
[86] PCT No.: PCT/JP91/00527
§ 371 Date: Dec. 20, 1991
§ 102(e) Date: Dec. 20, 1991
[87] PCT Pub. No.: WO91/16342
PCT Pub. Date: Oct. 31, 1991

[30] Foreign Application Priority Data

Apr. 20, 1990 [JP] Japan .................. 2-105047

[51] Int. Cl.$^5$ ............................. C07K 7/00
[52] U.S. Cl. ................................. 530/326
[58] Field of Search ........................ 530/326

[56] References Cited

PUBLICATIONS

Chemical Abstracts, vol. 115, No. 115, 1991.
Tawaragi et al., "Gene and Precursor Structure of Porcine C-type Natriuretic Peptide", Biochemical and Biophysical Research Communications, vol. 172, No. 2, Oct. 30, 1990, pp. 627–632.
Minamino et al., "N-Terminally Extended Form of C-Type Natriuretic Peptide (CNP-53) Identified in Porcine Brain", Biochemical and Biophysical Research Communications, vol. 170, No. 2, 1990, pp. 973–979.
Sudoh et al. Biochem. Biophys. Res. Comm. 168 (1990) 863–870.
Minamino et al. Biochem. Biophys. Res. Commun. 157 (1988) 402–409.

Primary Examiner—Merrell C. Cashion, Jr.
Assistant Examiner—Carol A. Salata
Attorney, Agent, or Firm—Cushman, Darby & Cushman

[57] ABSTRACT

Disclosed are a novel physiologically active peptide having the following structural formula and an acid addition salt thereof:

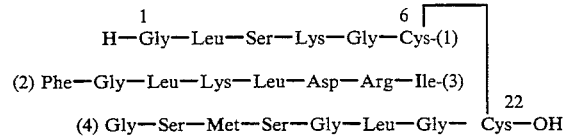

(where (1)/(2) and (3)/(4) are respectively bonded directly and each of the cysteine residues (Cys) at positions 6 and 22 forms an intramolecular S—S bond).

This novel peptide derives from porcine and since it exhibits natriuretic and hypotensive actions, the peptide is useful as a therapeutic for cardiac edema, nephredema, hepatic edema, hypertension, congestive heart failure, acute and chronic renal insufficiency, etc. Further, exhibiting the capability of suppressing the growth of smooth vascular muscle cells and the cGMP producing activity, the novel peptide is anticipated to have the potential for serving as an effective therapeutic for atherosclerosis.

1 Claim, 5 Drawing Sheets

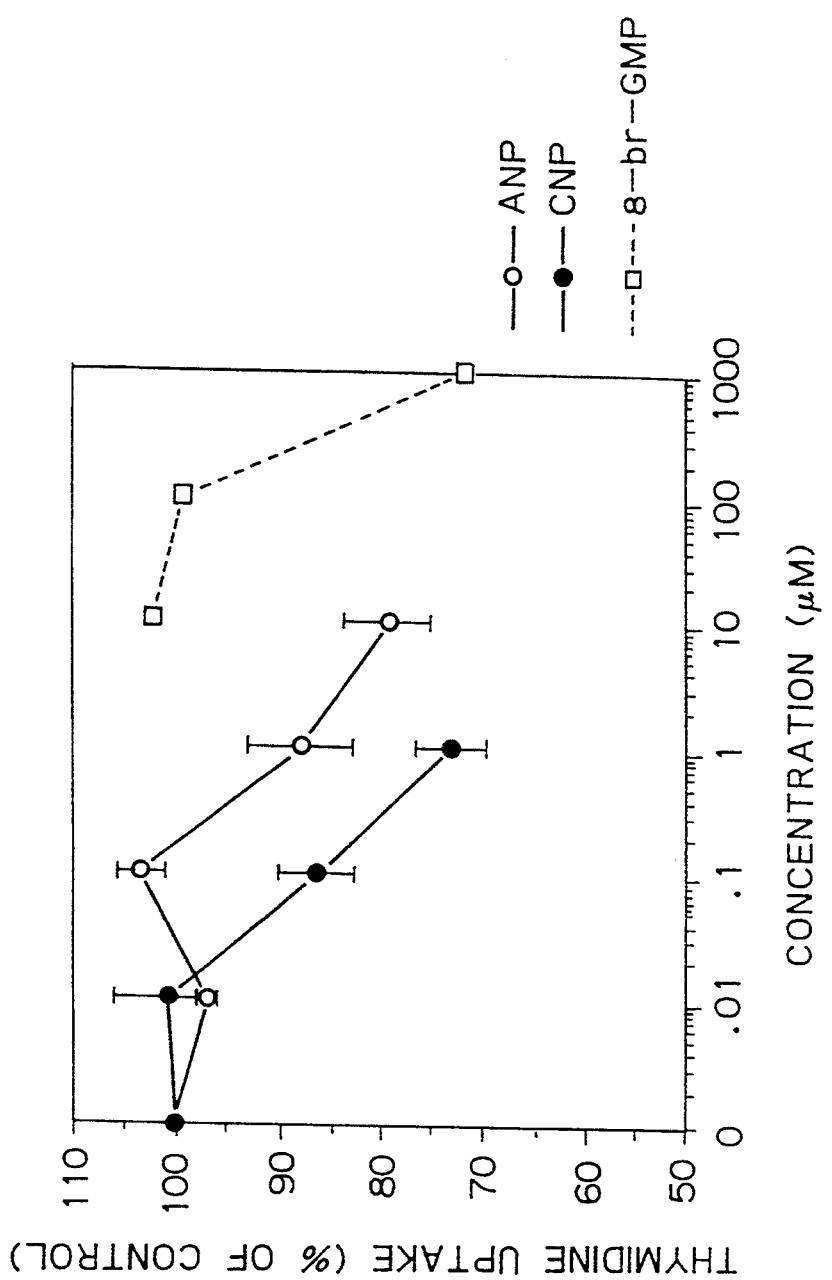

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ser Leu Arg Arg Ser Ser Cys Phe Gly Gly Arg Met Asp Arg Ile Gly
 1               5                  10                      15

Ala Gln Ser Gly Leu Gly Cys Asn Ser Phe Arg Val
            20                  25
```

( 2 ) INFORMATION FOR SEQ ID NO:2:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Asp Ser Gly Cys Phe Gly Arg Arg Leu Asp Arg Ile Gly Ser Leu Ser
 1               5                  10                      15

Gly Leu Gly Cys Asn Val Leu Arg Arg Tyr
            20                  25
```

( 2 ) INFORMATION FOR SEQ ID NO:3:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide (x i) SEQUENCE DESCRIPTION: SEQ ID NO:3:

Gly Leu Ser Lys Gly Cys Phe Gly Leu Lys Leu Asp Arg Ile Gly Ser
 1           5                  10                  15
Met Ser Gly Leu Gly Cys
            20

PORCINE DERIVED NOVEL PHYSIOLOGICALLY ACTIVE PEPTIDE

TECHNICAL FIELD

This invention relates to a novel porcine derived physiologically active peptide (CNP) having natriuretic and hypotensive actions, as well as the capability of suppressing the growth of vascular smooth muscle cells.

BACKGROUND ART

Two kinds of peptide hormones, named "atrial natriuretic peptide (ANP)" and "brain natriuretic peptide (BNP)", have recently been isolated from mammalian atria and brains as hormones that regulate the homeostatic balance of body fluid volume and blood pressure. The structures of those peptides and the mechanism of their biosynthesis have been unravelled and their physiological actions are also being unravelled.

ANP was first isolated from the human atrium in three types, α-type having a molecular weight of ca. 3000 (α-hANP), β-type of ca. 6000 (β-hANP) and γ-type of 13000 (γ-hANP), and their respective structures were unravelled (Kangawa, K. et al., Blochem. Biophys. Res. Commun., 118, 131, 1984; Kangawa, K. et al., Nature, 313, 397, 1985).

As a result, the following facts have been determined: (1) α-hANP is a single-stranded peptide that consists of 28 amino acids having a single S-S bond in the molecule; (2) β-hANP is an antiparallel dimer having an S-S bond formed between the molecules of γ-hANP; and (3) γ-hANP is a high-molecular weight protein composed of 126 amino acids, with α-hANP being contained in the C-terminal portion.

Further, analysis of the cDNA coding for α-hANP has shown that each of those three types of hANP (α-, β- and γ-hANP) is biosynthesized from the same precursor protein (Oikawa, S. et al., Nature, 309, 724, 1984). Stated more specifically, those peptides are first biosynthesized in atrial cells as a precursor (pre-hANP) composed of 151 amino acid residues and then, the signal peptide composed of 25 N-terminal residues is cleaved in the Golgi body to produce γ-hANP. Subsequently, the γ-hANP is further cleaved with an enzyme (i.e., subjected to processing) for transformation to α-hANP, which is secreted primarily into blood. The process of β-hANP synthesis still remains unclear today but most probably it is produced by way of α-hANP.

Ever since the structure of hANP was first unravelled, the structures of ANPs derived from other mammals have also been studied. And, today, the following knowledge is available: ANPs have similar amino acid sequences over a broad spectrum of mammals ranging from rodents to humans; in particular, α-type ANP (α-ANP) has the same amino acid sequence in higher mammals including humans, dogs and pigs; and α-type ANPs derived from rats and rabbits have entirely the same amino acid sequence as α-hANP except that the methionine residue in position 12 is replaced by an isoleucine residue (Oikawa, S. et al., Blochem, Biophys. Res. Commun., 132, 892, 1985; Forssmann, W.G. et al., Anat. Embryol., 168, 307, 1983).

When the distribution of ANP in vivo was examined using anti-α-hANP antisera, it was found that ANP also occurred in the brain, though in small amounts, as well as in the atrium. Further, ANP-containing neurons have been reported to occur in the hypothalamus and pontine tegmentum of the brain (Cantin, M. et al., Itistochemistry, 80, 113, 1984; Saper, C.B., et al., Science, 227, 1047, 1985) and, therefore, it is speculated today that ANP may also work in the brain as a nerve transmitter that participates in the regulation of the cardiovascular system.

Recently, a new peptide that was similar in structure to ANP but that was clearly distinguishable from the latter was isolated and identified from porcine brain and, like ANP, this peptide was verified to have natriuretic and hypotensive actions and hence was named "BNP" (Sudoh, T. et al., Nature, 332, 78, 1988). It was later found that porcine-derived BNP (pBNP) was a single-stranded peptide composed of 26 amino acids having a single S—S bond in the molecule. Further, a cDNA coding for human BNP was isolated and the structure of tile BNP precursor also became clear, showing that BNP was constructed from an entirely different precursor than in the case of ANP (Sudoh, T. al al., Biochem. Biophys. Res. Commun., 159, 1427, 1989). As of today, the structure of rat BNP has also been unravelled (Kojima, M. et al., Biochem. Biophys. Res. Commun., 159, 1420, 1989).

It was also found that BNP was present in porcine brain in an amount ten times higher than ANP and this suggested a higher possibility that in the brain BNP would work as a nerve transmitter for the nerve system to regulate the homeostatic balance of body fluid volume and blood pressure (Ueda, S. et al., Blochem. Biophys. Res. Commun., 155, 733, 1988).

It was later found that like ANP, BNP occurred not only in the brain but also in the atrium (though in an amount of only 2- 3% of ANP) to be secreted into blood, showing that like ANP, BNP was also a hormone regulating the homeostatic balance of body fluid volume and blood pressure (Minamino, N. et al., Blochem. Biophys. Res. Commun., 155, 740, 1988: Aburaya, M. et al., Biochem. Biophys, Res. Commun., 165, 872, 1989). As a matter of fact, it has been verified with experimentation on rats that pBNP has comparable levels of natriuretic and hypotensive actions to α-hANP. Thus, it has been found to date that at least two obviously different types (ANP and BNP) of hormones occur in mammals and that they regulate the homeostatic balance of body fluid volume and blood pressure. These peptides are secreted from the atrium into blood and work as hormones that regulate the homeostatic balance of body fluid volume and blood pressure. Further, it has been found that those peptides also occur in the brain, where they work as nerve transmitters for the nerve system to regulate the homeostatic balance of body fluid volume and blood pressure. At the same time, the studies conducted to date have shown that three kinds of receptor eDNA are cloned to those peptides and their structures have been identified. Two of the three receptor types have a guanylate cyclase domain in a intracellular portion of the molecule and the other type, which is generally referred to as a C-receptor (clearance receptor), does not have a guanylate cyclase domain in a intracellular portion of the molecule (Chinkers, M. et al., Nature, 338, 78, 1989; Chang, M.S. et al., Nature, 341, 68, 1989; Schulz et al., Cell, 58, 1155, 1989; Fuller, F. et al., J. Biol. Chem., 263, 9395, 1988).

However, as of today, the relationships between those receptors and the ligands (ANP, BNP) have not been clearly established. In other words, much still remains unclear about the relationships between the individual receptors and the physiological actions developed, as well as the specificity between ligand and receptor.

With all points of the foregoing discussion taken into account, the question arises as to whether ANP and BNP known today are the only hormones in mammals that regulate the homeostatic balance of body fluid volume and blood pressure. In particular, considering the aforementioned versatility of receptors, there is a high possibility that a new third peptide hormone (novel ligand) might exist aside from ANP and BNP.

However, as of today, whether any such novel ligand exists remains unclear.

Therefore, the object of the present invention is to isolate from mammals a novel peptide hormone that exhibits physiological activities (e.g. natriuretic and hypotensive actions) similar to ANP and BNP already known in mammals but which is clearly distinguishable from them and to establish a method of presenting said peptide to the industry.

DISCLOSURE OF THE INVENTION

The present inventor noted that when isolating and purifying ANP and BNP, relaxant activity measurements using chick rectum samples were useful as a comparatively simple and yet reliable method of bioassay and planned a project for discovering a novel peptide hormone having natriuretic and hypotensive actions from porcine brain using the result of said bioassay as an indicator.

In the present invention, porcine brain was first homogenated in a suitable acidic solvent, say, glacial acetic acid and, with this used as a starting material, peptide fractions having molecular weights of ca. 3000 were purified, with the results of the aforementioned bioassay used as an indicator, by combinations of various techniques conventionally used in peptide purification. As a result, a peptide having relaxant activity in a bioassay system using chick rectum samples could successfully be purified to a homogeneous and pure state as shown in FIG. 2. In the next place, part of this peptide was reduced and the cysteine residues in that the peptide was carboxymethylated and its amino acid composition was determined, showing that it was a peptide composed of 22 amino acid residues containing 2 cysteine residues as shown in Table 1 below. Further, this peptide was determined for its primary amino acid sequence, with it being finally found to be a novel peptide having the following structure:

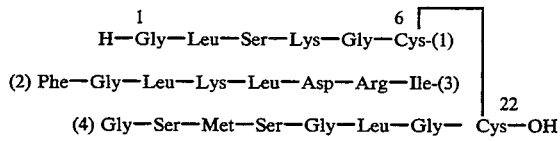

(where (1)/(2) and (3)/(4) are respectively bonded directly and each of the cysteine residues (Cys) at positions 6 and 22 forms an intramolecular S-S bond).

The novel peptide is hereinafter referred to as "CNP (C-type natriuretic peptide)".

When CNP was compared with porcine derived α-ANP and BNP as regards the primary amino acid sequence and structure (see FIG. 4), it was found that each of those peptides formed a ring structure that had a single S—S bond in the molecule and that was composed of 17 amino acid residues; it was also found that the primary amino acid sequence forming this ring structure was highly homologous among CNP, α-ANP and BNP, with 12 of the 17 amino acid residues being the same amino acid residues.

However, except for that cyclic structural portion, CNP has an entirely different structure from α-ANP or BNP in the N- and C-terminal portions. What is particularly characteristic is the structure in the C-terminal portion; the C-terminal portions of α-ANP and BNP have a "tail" structure in which a few additional amino acid residues are attached to the cysteine residue forming the ring structure, whereas the C-terminus of CNP is a cysteine residue at position 22, with no "tail" structure being present. Further, CNP has no observable homology to α-ANP or BNP as regards the primary amino acid sequence in the N-terminal portion. From these facts, it has been found that in spite of its structural similarity to heretofore known α-ANP or BNP, CNP is a novel peptide that is obviously different.

Further, in view of its structural similarity to α-hANP or BNP, the present inventor thought that CNP might exhibit natriuretic and hypotensive actions and administered it to the vein of rats for investigating the occurrence of natriuretic and hypotensive actions. It was found that CNP obviously had those actions (see Table 2) and the present invention was completed. Thus, the present inventor conducted intensive-studies with a view to finding from mammals a novel peptide hormone that had physiological activities (e.g. natriuretic and hypotensive actions) similar to those of ANP and BNP already known in mammals but which was structurally distinguishable therefrom; as a result, the inventor successfully isolated a novel peptide (CNP) of 22 amino acid residues from porcine brain and determined the structure of that peptide at the same time, the inventor found that this peptide had outstanding natriuretic and hypotensive actions, on the basis of which the present invention has been accomplished.

The present inventor also found that the peptide of this invention had a growth inhibiting action on a cultured vascular smooth muscle cell line and, further, it was found to have an activity for promoting the production of cyclic guanosine monophosphate (cGMP) which is considered to be a second messenger for the relaxant action in the same system. Considering those activities, i.e., the ability to suppress the growth of vascular smooth muscle cells and the cGMP producing activity, it is anticipated that the peptide of the present invention can potentially be used as an effective agent for treating atherosclerosis.

As described on the foregoing pages, the peptide of the present invention or salts thereof have not only a good smooth muscle relaxant action but also uretic and natriuretic actions, as well as hypotensive action; hence, they may be useful as therapeutics for various diseases such as cardiac edema, nephredema, hepatic edema, hypertension, congestive heart failure, acute and chronic renal insufficiency, etc.

The peptide of the present invention may be in the form of salts with metals such as sodium, potassium, lithium and calcium, or salts with organic bases. It may also take the form of salts with mineral acids such as sulfuric acid, hydrochloric acid and phosphoric acid, or salts with organic acids such as acetic acid and maleic acid. If the peptide according to the present invention is to be used as a medicine, it may of course be in a free form or a pharmaceutically acceptable salt.

The peptide of the present invention or its pharmacologically acceptable salt is preferably mixed with a pharmacologically acceptable carrier, excipient, diluent, etc. that are known per se before they are administered by methods that are commonly used with peptide drugs, namely, by parenteral administration such as intravenous, intramuscular or subcutaneous administration. When administered perorally, the medical composition of the present invention is subject to degradation in the digestive tract and, hence, this method of administration usually is not effective. However, it may be administered perorally as a preparation that is resistant to degradation in the digestive tract, for example, as a microcapsule in which the peptide of the present invention is incorporated as the active ingredient in liposome. Another method of administration that can be adopted is to have the drug absorbed through the mucous membrane other than in the digestive tract such as in the rectum, within the nose or beneath the tongue. In this case, the drug can be administered as a suppository, intranasal spray or sublingual tablets.

The dose of the medical composition of the present invention may vary with tile type of disease, the age of patient, his body weight, the severity of disease, the route of administration, etc; typically, it can be administered in a dose in the range of 0.1 μg/kg–100 mg/kg, preferably in the range of 0.5 μg/kg–5 mg/kg, more preferably 1 μg/kg–1 mg/kg.

In the examples to be described below, CNP was isolated and purified from porcine brain; however, since the structure of CNP has been unravelled in the present invention, it goes without saying that CNP can be readily produced by well known methods of chemical synthesis or gene manipulation.

BRIEF DESCRIPTION OF DRAWINGS

FIG. 5 is a graph showing the activity of CNP, ANP and 8-br-cGMP in blocking thymidine uptake.

The present invention is described below in detail by means of examples.

EXAMPLE 1:

Isolation and purification of CNP from porcine brain

Figure 1:
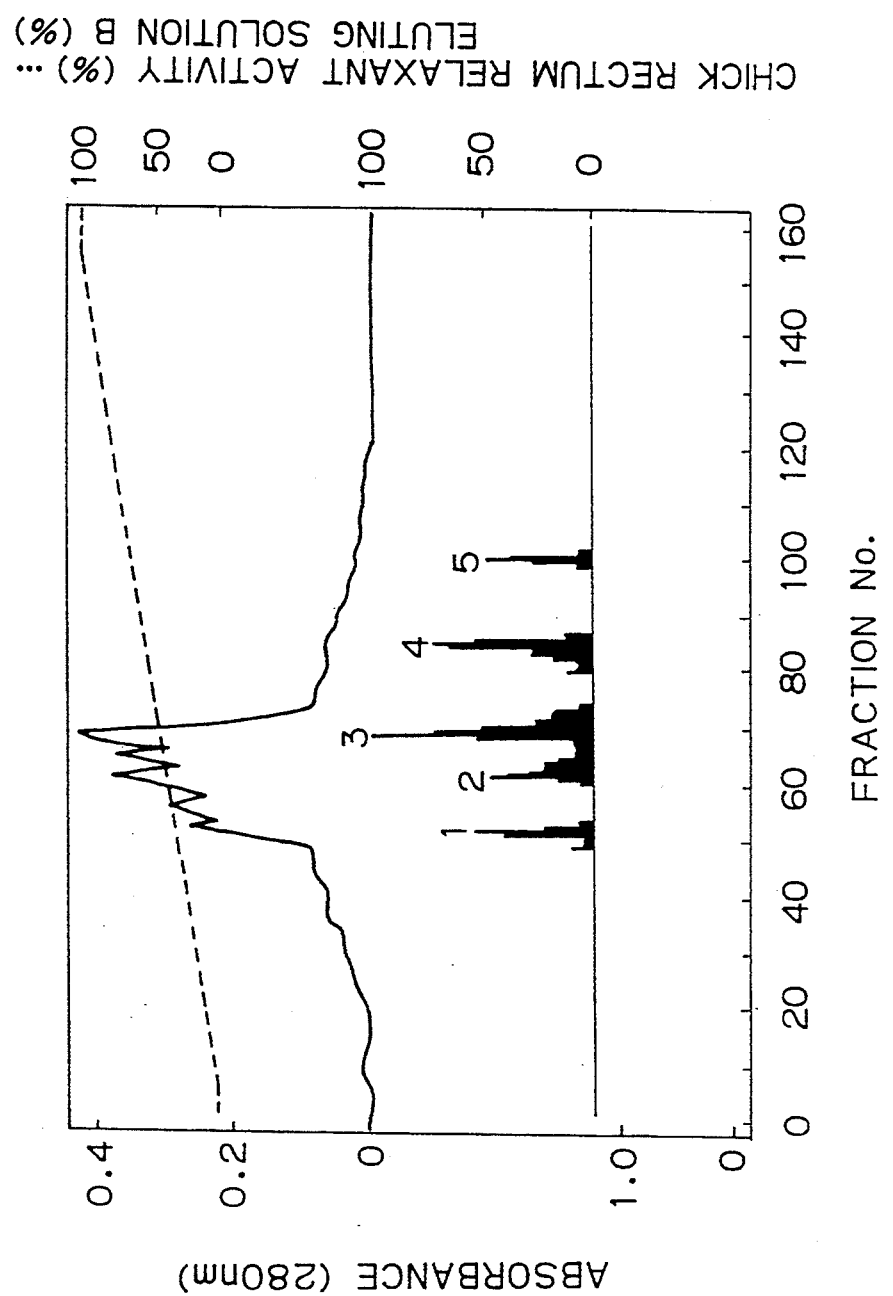
FIG. 1 is a graph showing the elution profile obtained when an extract from porcine brain (i.e., peptide fractions of molecular weights of ca. 3000 that were obtained by fractionating SP-III fractions on Sephadex G-50 and G-25) was further purified by CM ion-exchange chromatography, as well as the chick rectum relaxant activity of the resulting fractions.
Figure 2:
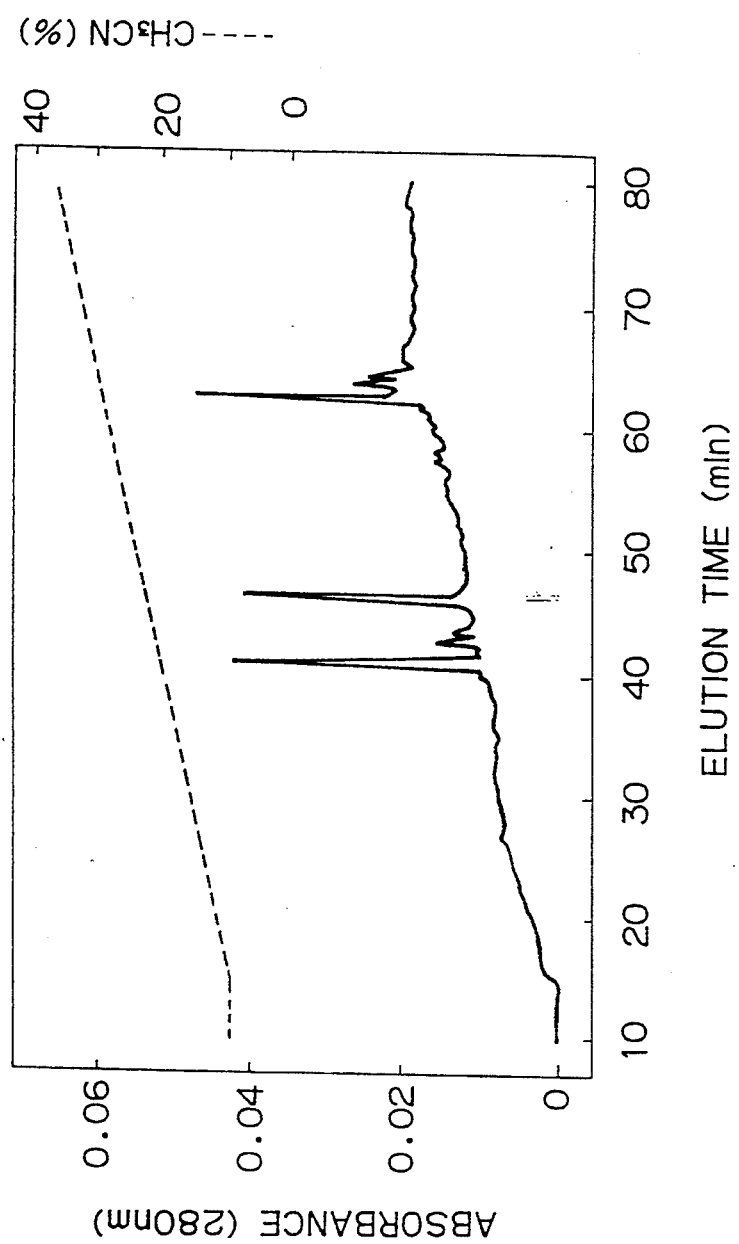
FIG. 2 is a chart showing the elution profile of reverse-phase ItPLC used for final purification of CNP, as well as the chick rectum relaxant activity of the resulting fractions.

Forty kilograms of brain was extracted from 480 swines, shreded and had the protease inactivated by treatment with 2 volumes of boiling water for 5 min. After cooling, glacial acetic acid was added to give a final concentration of 1 M. The thus treated tissue was homogenized with a Polytron mixer. Subsequently, the homogenate was centrifuged to be divided into a precipitate fraction and a supernatant fraction, which was concentrated with a pallicon cassette (PCAC #000-05, Millipore). Acetone was added to the concentrate (final concentration, 66%) and the resulting precipitate was removed by centrifugation, with the supernatant being subsequently concentrated under vacuum. The resulting concentrate was dissolved in 0.5 M acetic acid and the solution was loaded onto a C-18 silica gel column (capacity, 1.5 l; LC-SORB SPW-C-0DS, Chemco) in four divided portions. The peptides adsorbed on the column were eluted with a solution prepared from water, acetonitrile ($CH_3CN$) and 10% trifluoroacetic acid (TFA) in a ratio of 40:60:1 (v/v). By concentrating the eluate, a residue containing peptides in a dry weight of 26 g was obtained. One half the amount of this residue was dissolved in 1 M acetic acid and subjected to ion-exchange chromatography on an SP-Sephadex C-25 column ($H^+$-form, 3×38 cm) equilibrated with 1 M acetic acid. The peptides adsorbed on the column were successively eluted with 1 M acetic acid, 2 M pyridine and 2 M pyridine-acetic acid (pit 5.0) in the order written. The thus obtained fractions were designated SP-I, SP-II and SP-III, respectively, and lyophilized. The thus obtained fraction SP-ZII (dry weight, 5.2 g) was subjected to gel filtration on a Sephadex G-50 column (fine, 7.5×145 cm, Pharmacia), whereby fractions containing peptides with molecular weights of ca. 1000–5000 were obtained in a dry weight of 2.96 g. Further, these fractions were subjected to gel filtration on a Sephadex G-25 column (fine, 7.5×150 cm, Pharmacia), whereby peptide fractions with molecular weights of ca. 3000 were obtained in a dry weight of 440 mg. Subsequently, these fractions were further fractionated by CM (CM-52, 2.4×52.5 cm, Whatman) ion-exchange chromatography (eluting solution A: 10 mM $HCOONH_4$ (pH 6.6)/$CH_3CN$=90/10 (V/V); eluting solution B: 0.5 M $HCOONH_4$ 8pH 6.6)/$CH_3CN$=90/10 (V/V); eluting condition: linear density gradient using eluting solutions A and B; flow rate: 35 ml/h; fraction size: 20 ml/tube) (see FIG. 1) and fractions #51–53 shown in FIG. 1 were collected. Subsequently, these fractions (29 mg) were subjected to immunoaffinity chromatography using an anti-ANP antibody (details of column preparation are described in the following report by the present inventors: Ueda, S. et al., Biochem. Biophys. Res. Commun., 1987, 149, 1055–1067) and the peptides adsorbed on the column were eluted with a 1 M acetic acid solution containing 10% $CH_3CN$. For final purification of the novel physiologically active peptide of the present invention, the peptide fractions adsorbed on the aforementioned immunoaffinity column were separated and purified by reverse-phase HPLC (flow rate: 1 ml/min; eluting solution A: $H_2O$/$CH_3CN$/10% TFA=90/10/1 (V/V); eluting solution B: $H_2O$/$CH_3CN$/10% TFA =40/60/1 (V/V); eluting condition: linear density gradient using eluting solutions A and B; eluting time: 120 min) using a diphenyl column (219 TP54, 4.6×250 mm, Vydac), and the resulting fractions were examined for relaxant activity on chick rectum samples. As a result, a peptide showing relaxant activity on chick rectum samples (see FIG. 2) could successfully be purified until it showed a single peak and it was designated "CNP". The yield of CNP was ca. 1 μg (400 pmol) starting from 40 kg of porcine brain.

EXAMPLE 2:

Determining the structure of CNP

A. S-Carboxymethylation of CNP

Three-fourths of the CNP obtained in Example 1 were subjected to reaction in 0.5 M Tris-HCl buffer (ptI 8.0) at 37° C. for 4 h using 50 mM dithiothreitol (DTT) and, then, 100 mM iodoacetate was added, followed by 5-min treatment to obtain (RCM) CNP, or an S-carboxymethylated product of CNP.

B. Determining the amino acid sequence of (RCM) CNP

About 150 pmol of (RCM) CNP obtained in Example 2.A was first treated with 6 N hydrochloric acid containing 0.1% phenol and 0.02% 2-mercaptoethanol at 110° C. for 24 h, whereby (RCM) CNP was hydrolyzed completely. Then, the sample was analyzed for the amino acid composition of (RCM) CNP using an amino acid analyzer (L-8500 of Hitachi, Ltd.) The obtained data were as shown in Table 1, indicating that the CNP of interest was a peptide composed of 22 amino acid residues containing 2 cysteine residues. Table 1 shows the amino acid sequence of (RCM) CNP. The values in parentheses are the nearest integers to the measured values, and CmCys represents S-carboxymethylcysteine.

TABLE 1

| (RCM) CNP | | |
|---|---|---|
| CmCys | 1.67 | (2) |
| Asp | 1.23 | (1) |
| Ser | 2.78 | (3) |
| Gly | 6.03 | (6) |
| Met | 0.88 | (1) |
| Ile | 1.00 | (1) |
| Leu | 4.01 | (4) |
| Phe | 0.96 | (1) |
| Lys | 2.10 | (2) |
| Arg | 1.14 | (1) |
| Total | | (22) |

C. Determining the primary amino acid sequence of (RCM) CNP

Figure 3:
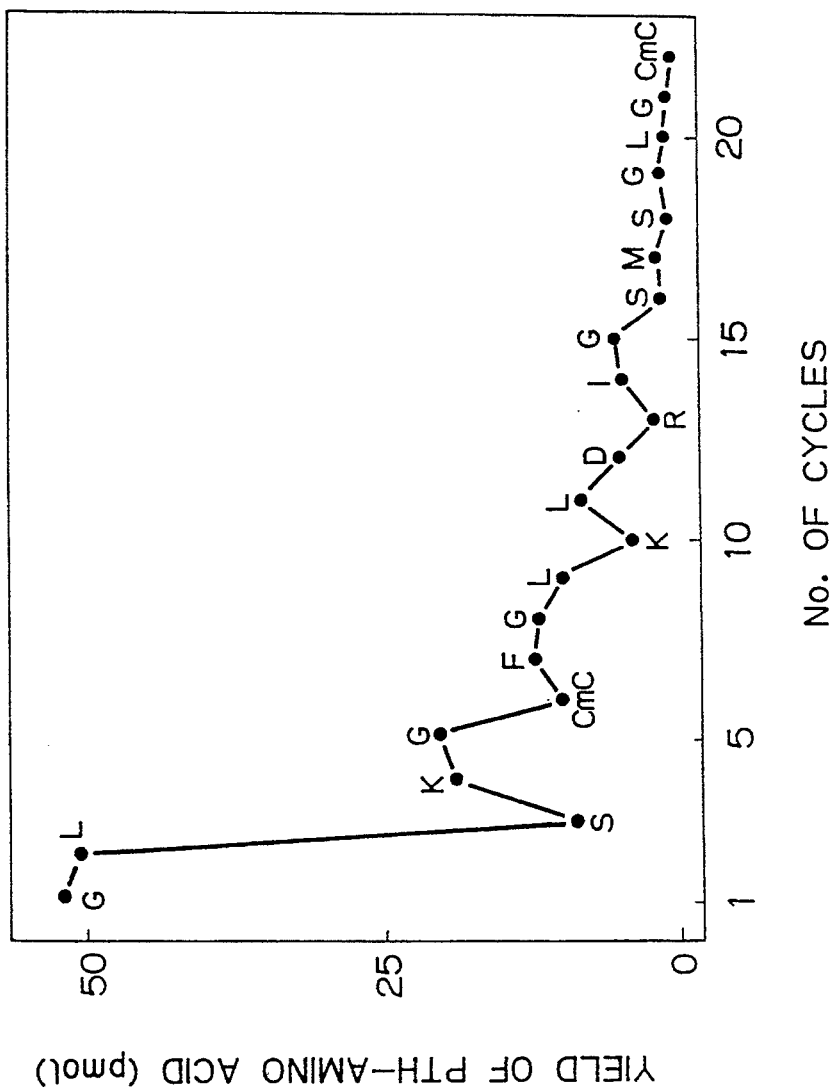
FIG. 3 is a graph showing the yield of PTH-amino acid that was produced at successive cycles of the Edman degradation of (RCM) CNP, as well as the amino acid sequence of that PTH-amino acid; each amino acid is represented by one word declared and Cm stands for an S-carboxymethylcysteine residue.
Figure 4:
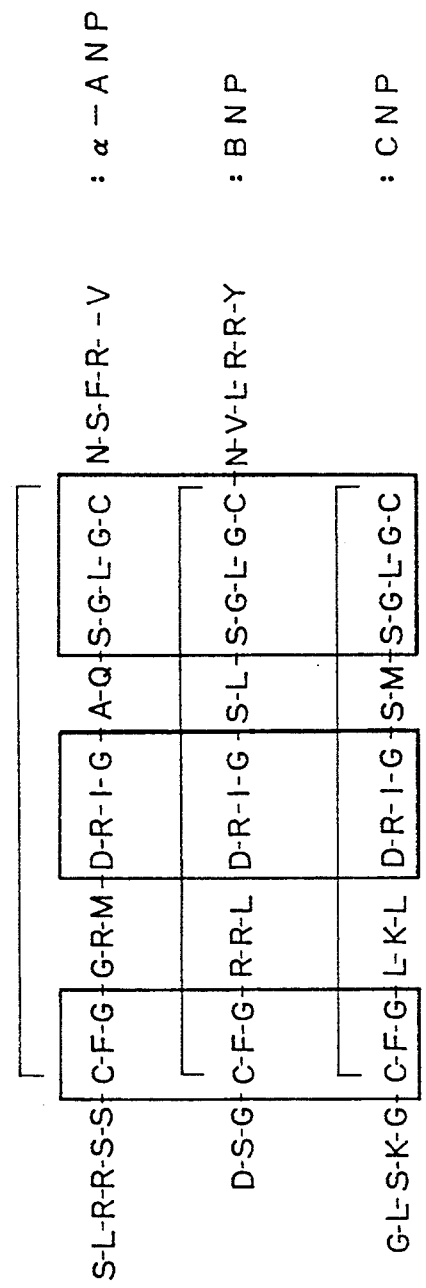
FIG. 4 is a chart showing the primary amino acid sequences of porcine α-hANP (see SEQ ID NO:1) BNP (see SEQ ID NO:2) and CNP (see SEQ ID NO:3), as well as the homology among the primary amino acid sequences of those peptides.

About 150 pmol of (RCM) CNP prepared in Example 2.A was loaded in an automatic amino acid sequencer (Applied Biosystems 470A/120A) and the primary amino acid sequence was analyzed by Edman degradation. The results were as shown in FIG. 3, enabling one to determine the primary amino acid sequence of (RCM) CNP.

D. Chemical synthesis of CNP and identification of S-S binding mode

The primary amino acid sequence determined in Example 2.C was used as a basis for synthesizing CNP by a solid-phase synthesis method with a peptide synthesizer (Applied Biosystems 430A).

In the synthesis, 4-methylbenzyl was used as a group for protecting StI in cysteine groups and HF was used to achieve complete deprotection, followed by treating SH groups in the cysteine residues in positions 6 and 22 of CNP with potassium ferricyanide [$K_3Fe(CN)_6$] to form an intramolecular S-S bond. The structure of the CNP thus synthesized was checked by amino acid analysis and by analyzing the primary amino acid sequence.

Further, the chemically synthesized CNP was in complete agreement with the naturally occurring CNP of Example 1 in terms of elution time on HPLC, so it was finally determined that CNP had the structure:

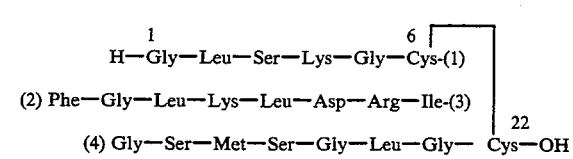

(where (1)/(2) and (3)/(4) are respectively bonded directly and each of the cysteine residues (Cys) at positions 6 and 22 forms an intramolecular S—S bond).

EXAMPLE 3:

Biological Properties of CNP

A. Chick rect-m relaxant activity of CNP

Chick rectum relaxant activity was measured in accordance with the method of Curtie et al. (Cuttle et al., Nature, 221, 1–13, 1983). In this system of measurement, CNP exhibited ca. 3 - 4 times as high activity as α-hANP.

B. Natriuretic and hypotensive actions of CNP

Male SD rats (body weight: 230–290 g) were anesthetized by intraperitoneal injection with 65 mg/kg of pentobarbital and fitted with a tracheotomy tube (PE-240 of Clay Adams) in order to insure the respiratory tract. A cannula (PE-50) for blood pressure measurement was inserted into the hip artery and a Ringer's solution was injected at a steady rate of 1.8 ml/hr through a cannula (PE-10) inserted into the hip vein. A urinary sample was taken into a test tube through a cystic cannula in the form of a Silastic tube (i.d. 0.02 inch; o.d. 0.037 inch; Dow Corning). Urinary samples were taken both for 15 minutes before the administration of the test substance and until 15 minutes after the administration at 5 min interval, followed by subsequent sampling at predetermined time intervals. By comparing the amount of each sample with the concentration of an electrolyte in it, as well as by measuring the blood pressure changes, the actions of the test substance were evaluated.

The test substance CNP was dissolved in a predetermined amount in 0.1 N acetic acid and thereafter neutralized with a 1/10 volume of 1.3 M Tris solution. The sample was diluted with 50 μl of sterilized physiological saline and administered via the cervical vein. As shown in Table 2, CNP was found to exhibit natriuretic and hypotensive actions and it was also found that those actions increased in a dose-dependent manner.

Table 2 shows the natriuretic and hypotensive actions of CNP.

TABLE 2

| CNP dose (nmol/kg) | Urine excretion % | $Na^+$ excretion % | $K^+$ excretion % | $Cl^-$ excretion % | Blood pressure drop (mmHg) |
|---|---|---|---|---|---|
| 12 | 229 ± 38 | 192 ± 28 | 220 ± 43 | 228 ± 32 | 6.7 ± 1.7 |
| 80 | 251 ± 62 | 286 ± 125 | 167 ± 29 | 301 ± 83 | 16.7 ± 4.2 |
| 160 | 421 ± 40 | 371 ± 69 | 238 ± 46 | 400 ± 45 | 14.2 ± 5.2 |

Data are shown in terms of mean±S.D., as obtained from each group of 4 animals, of the change that occurred in the 15-min period from the administration of the test substance, as compared to the state before the administration.

C. Measurement of cell growth suppressing activity

Cell growth suppressing ability was evaluated in accordance with the method of Kariya et al. (Atherosclerosis, 80, 143–147, 1990) by measuring the uptake of $^3$H thymidine into cells as an indicator of DNA synthesis activity using VSMC of rats. Cells tuned to a stationary phase were incubated in 1% serum at 37° C. for 14 h together with various concentrations of α-hANP or CNP; following the addition of 37 KBq/ml [$^3$H]thymidine, the incubation was continued for another 4 h. The radioactivity of [$^3$H] thymidine incorporated into the cells was measured. The values of measurement were such that the radioactivity of [$^3$H] thymidine for the case where only 1% serum was added in the absence of peptide was taken as 100%, with the percent suppression due to the peptide at the respective concentrations being accordingly calculated.

The results are shown in FIG. 5.

Industrial Applicability

As described hereinabove, the present inventor succeeded in isolating and purifying a novel physiologically active peptide from porcine brain using chick rectum relaxant activity as an indicator; the inventor not only determined the structure of this peptide but also found that this peptide had natriuretic and hypotensive actions. In short, the present invention unveiled the existence of a third hormone in mammals besides and and BNP which were already known as hormones regulating the homeostatic balance of body fluid volume and blood pressure, and this will make a great contribution to future efforts to unravel the mechanism by which the homeostatic balance between body fluid volume and blood pressure is maintained in mammals.

Further, in consideration of its nature to exhibit the capability of suppressing the growth of vascular smooth muscle cells and the cGMP producing activity, the peptide of the present invention is anticipated to have the potential for serving as an effective therapeutic for atherosclerosis.

---

I claim:

1. An isolated novel physiologically active peptide having the following structural formula and an acid addition salt thereof:

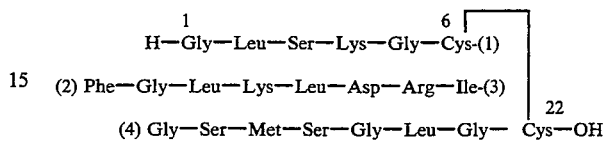

where (1)/(2) and (3)/(4) are respectively bonded directly and each of the cysteine residues (Cys) at positions 6 and 22 forms an intramolecular S—S bond.

* * * * *